(12) United States Patent
Tufts et al.

(10) Patent No.: US 6,991,394 B2
(45) Date of Patent: Jan. 31, 2006

(54) LIQUID APPLICATOR WITH A MECHANISM FOR FRACTURING MULTIPLE AMPOULES

(75) Inventors: Scott A. Tufts, El Paso, TX (US); Manual Guzman, El Paso, TX (US); Jesus Flores, El Paso, TX (US)

(73) Assignee: Medi-Flex, Inc., Overland Park, KS (US)

( * ) Notice: Subject to any disclaimer, the term of this patent is extended or adjusted under 35 U.S.C. 154(b) by 32 days.

(21) Appl. No.: 10/748,896

(22) Filed: Dec. 30, 2003

(65) Prior Publication Data

US 2004/0179888 A1 Sep. 16, 2004

Related U.S. Application Data

(60) Provisional application No. 60/439,197, filed on Jan. 10, 2003.

(51) Int. Cl.
*B43K 5/14* (2006.01)
*B05C 21/00* (2006.01)

(52) U.S. Cl. ........................ 401/134; 401/133; 401/196

(58) Field of Classification Search ........ 401/132–135, 401/205, 206, 183, 184, 186, 44, 47; 604/1–3; 222/541.1, 541.3
See application file for complete search history.

(56) References Cited

U.S. PATENT DOCUMENTS

| | | | | |
|---|---|---|---|---|
| 1,332,985 | A | * | 3/1920 | Jarrett ........................ 206/222 |
| 3,704,072 | A | * | 11/1972 | Kaufman .................... 401/291 |
| 4,784,506 | A | | 11/1988 | Koreska et al. |
| 4,925,327 | A | | 5/1990 | Wirt |
| 5,256,537 | A | | 10/1993 | Phillips et al. |
| 5,425,915 | A | | 6/1995 | Phillips et al. |
| 5,509,744 | A | * | 4/1996 | Frazier ....................... 401/132 |
| 5,772,346 | A | | 6/1998 | Edwards |
| 5,775,826 | A | | 7/1998 | Miller |
| 5,791,801 | A | | 8/1998 | Miller |
| 6,039,488 | A | * | 3/2000 | Krawczyk et al. .......... 401/132 |
| 6,056,737 | A | | 5/2000 | Rosen |
| 6,340,097 | B1 | | 1/2002 | D'Alessio et al. |
| 6,371,675 | B1 | * | 4/2002 | Hoang et al. ............... 401/205 |
| 6,477,411 | B1 | | 11/2002 | Beck |
| 6,478,191 | B1 | | 11/2002 | D'Alessio et al. |
| 6,536,975 | B1 | * | 3/2003 | Tufts .......................... 401/134 |

* cited by examiner

*Primary Examiner*—David J. Walczak
(74) *Attorney, Agent, or Firm*—Shook, Hardy & Bacon LLP

(57) ABSTRACT

Liquid applicators having a flexible elongated hollow body are provided. More specifically, provided are hand-held liquid applications having a flexible elongated hollow body within which at least two liquid-filled, glass ampoules are received, and a mechanism for fracturing the ampoules to release the liquid for dispensing.

21 Claims, 4 Drawing Sheets

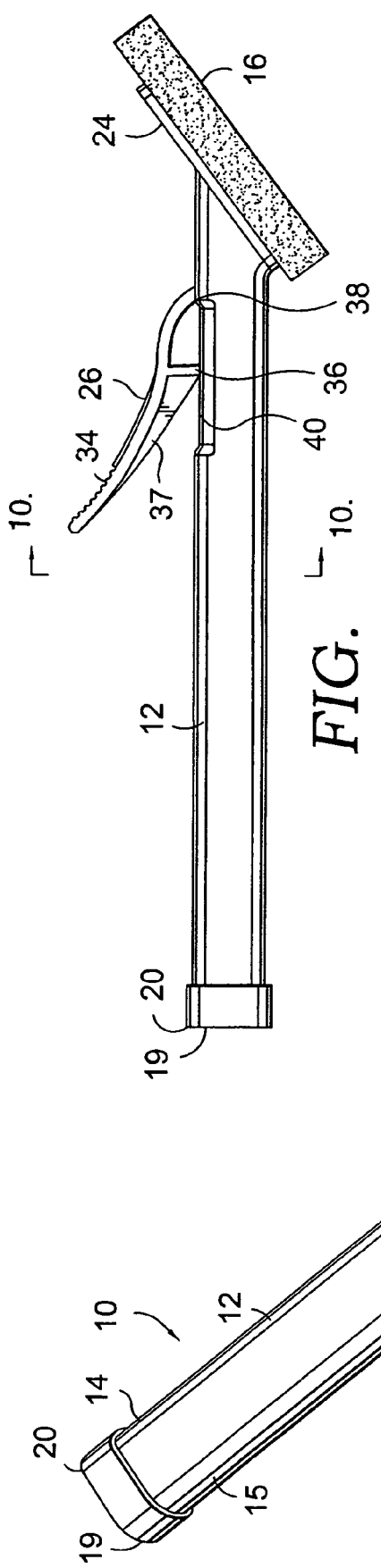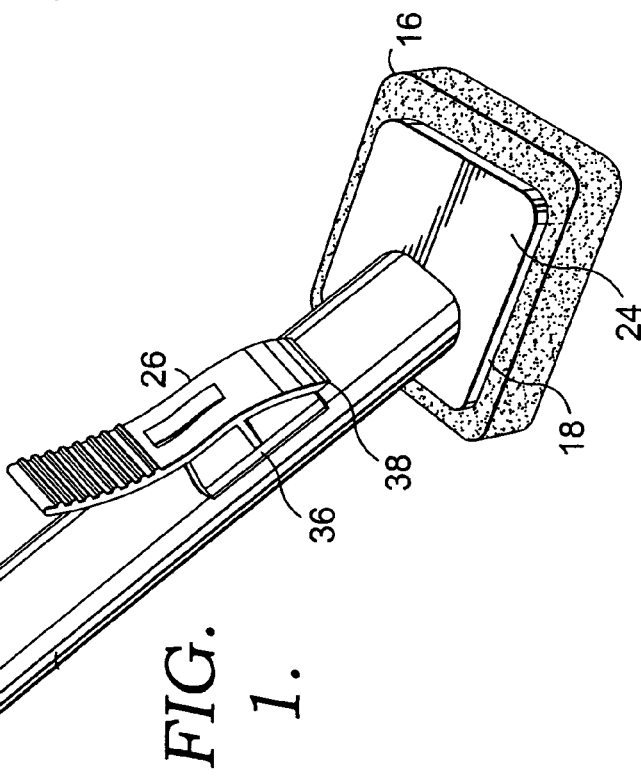

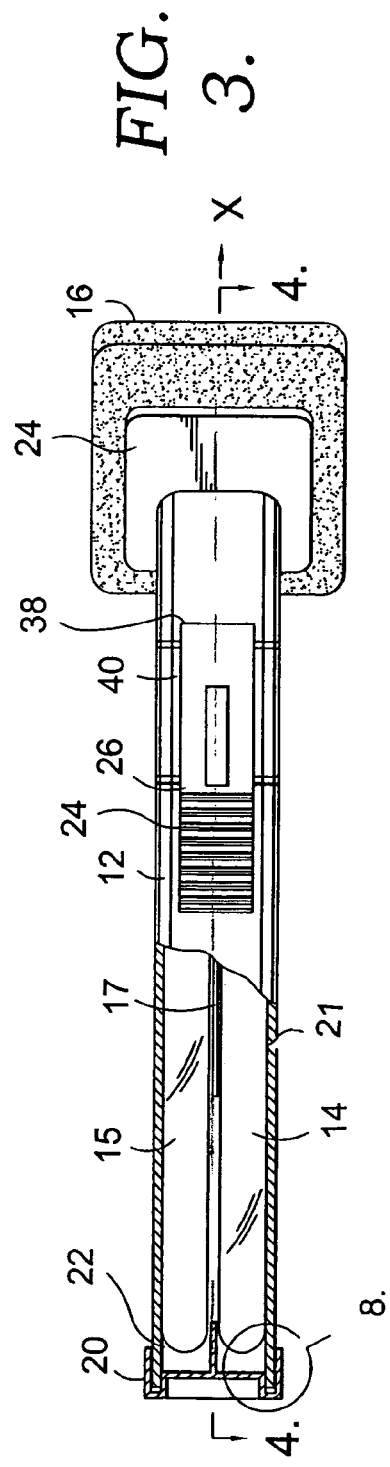
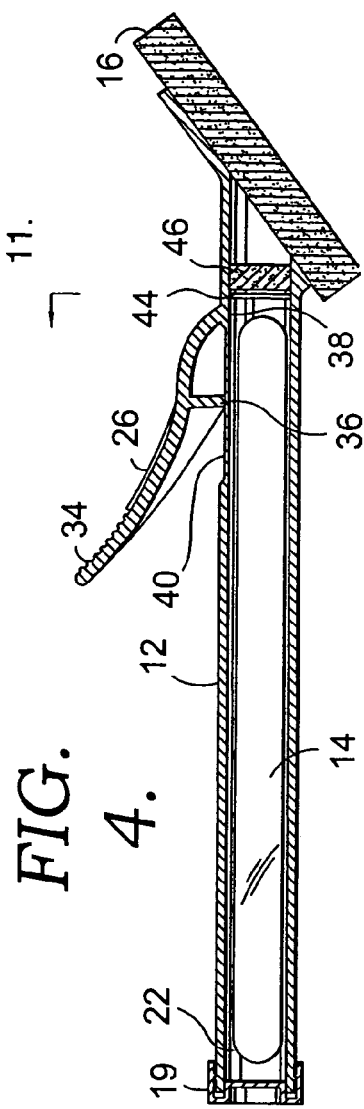

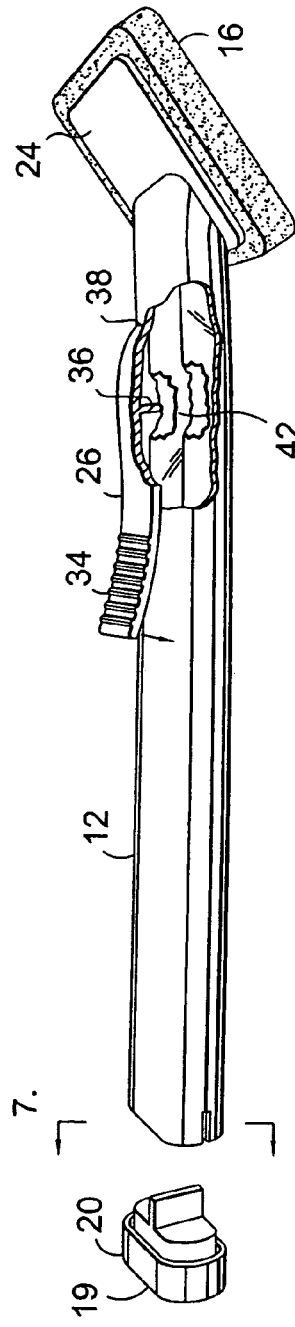
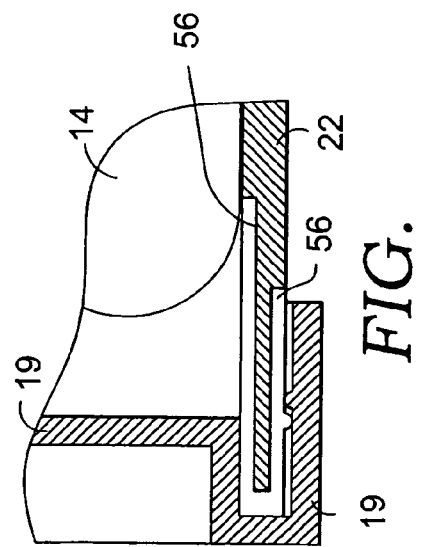
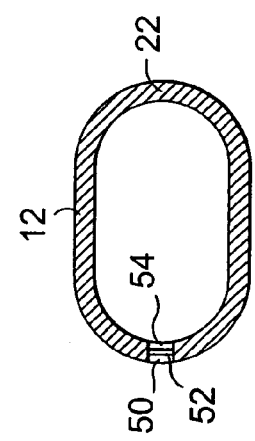
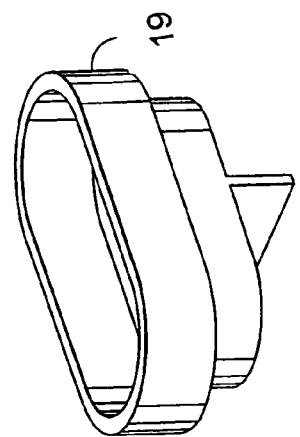
FIG. 5.
FIG. 6.
FIG. 7.
FIG. 8.

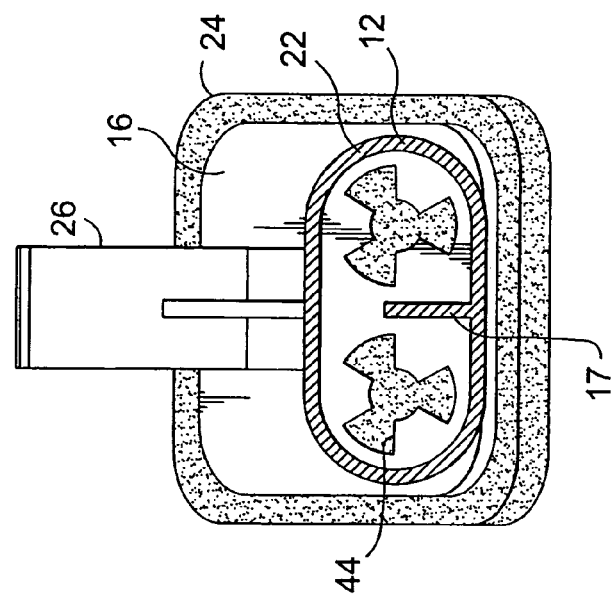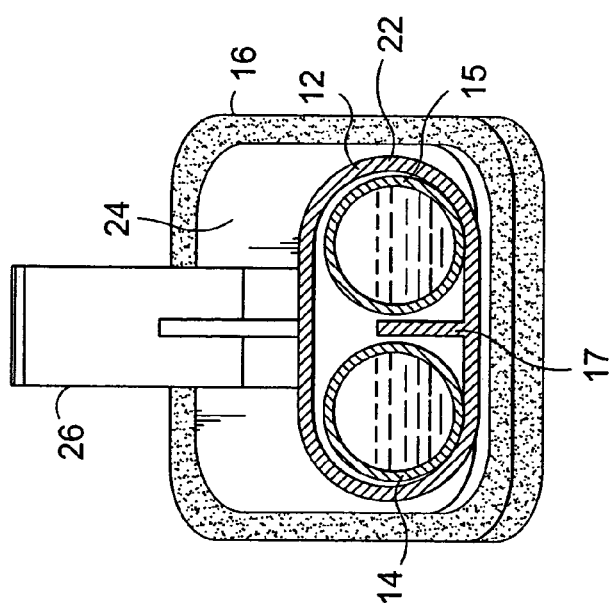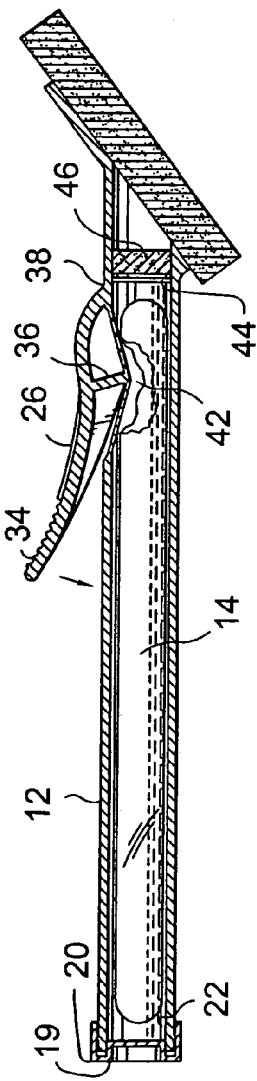

LIQUID APPLICATOR WITH A MECHANISM FOR FRACTURING MULTIPLE AMPOULES

CROSS-REFERENCE TO RELATED APPLICATIONS

This application claims the benefit of priority to U.S. Provisional Application No. 60/439,197 filed on Jan. 10, 2003.

STATEMENT REGARDING FEDERALLY SPONSORED RESEARCH OR DEVELOPMENT

Not Applicable.

FIELD OF THE INVENTION

The present invention relates generally to liquid applicators. More specifically, the present invention relates to a hand-held liquid applicator having a flexible elongated hollow body within which at least two liquid-filled, glass ampoules are received, and a mechanism for fracturing the ampoules to release the liquid for dispensing.

BACKGROUND OF THE INVENTION

Applicators for applying liquids such as medicaments or cleansing agents are known in the prior art. Conventional applicators typically provide a generally cylindrical body construction and include only one glass ampoule retained within the body; a sponge or tip secured to the body, at least one surface of which is exposed to the ampoule; and a means for fracturing the ampoule such that when the ampoule is fractured, the liquid stored therein is dispensed to the sponge for application.

Some prior art discloses more than one ampoule retained within the body of the applicator. In such applicators, the liquid-filled ampoules are typically fractured by the user grasping the body wall and exerting a squeezing force directly thereon. Of course, the squeezing force necessary to fracture two ampoules depends upon a number of factors such as the shape of the ampoule, the material of which the body and ampoules are formed, and the location at which the force is exerted.

Numerous problems are encountered with applicators of this type. For example, it is difficult to fracture more than one ampoule in this manner and may require a user employ both hands to break the ampoules dispensing the fluid. Furthermore, because so much effort is required to fracture more than one ampoule, it may be difficult for the user to fracture more than one ampoule at the same time.

Other prior art has revealed applicators with more than one ampoule and a mechanism for breaking the ampoules one at a time. Again, this requires that the user employ both hands to fracture more than one ampoule. Furthermore, breaking ampoules one at a time is inefficient and is not reliable.

In many situations, it is necessary for the user of a liquid dispenser of antiseptics or medicaments to use one hand to expose or position a portion of a patient's body which is to be treated with the liquid, while preparing the dispenser for use and applying the liquid with the other hand. For example, liquid applicators are often used to apply a pre-operative liquid, such as an isopropyl alcohol or iodine based solution, to an area of the body just prior to surgery. Thus, it is essential that the user be able to prepare and use the applicator with only one hand in order to enable the practical use thereof.

SUMMARY OF THE INVENTION

Accordingly, in one of its aspects, the present invention provides an improved hand-held liquid applicator of quality construction having a body with a mechanism that may be depressed to fracture more than one ampoule enclosed therein substantially simultaneously, releasing the liquid contained in the ampoules so that the liquid may be applied by the porous element attached to the body of the applicator.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means, instrumentalities and combinations particularly pointed out in the appended claims.

BRIEF DESCRIPTION OF THE DRAWINGS

In the accompanying drawings which form a part of the specification and are to be read in conjunction therewith, and in which like reference numerals are employed to indicate like parts in the various views:

FIG. 1 is a perspective view of a liquid applicator constructed in accordance with an embodiment of the invention;

FIG. 2 is a side plan view constructed in accordance with an embodiment of the invention;

FIG. 3 is a top plan view of a liquid applicator constructed in accordance with an embodiment of the invention with a portion of the applicator body removed to expose the inside of the body and the ampoules;

FIG. 4 is a side plan view of a liquid applicator constructed in accordance with an embodiment of the invention with a portion of the applicator body removed to expose the inside of the body and the ampoules;

FIG. 5 is a side plan view of a liquid applicator constructed in accordance with an embodiment of the invention with a portion of the applicator body removed to expose the two ampoules being fractured at substantially the same time by the lever;

FIG. 6 is a side plan view of a the cap of a liquid applicator constructed in accordance with an embodiment of the invention;

FIG. 7 is a fragmentary cross-sectional view taken generally across line 7—7 of FIG. 5;

FIG. 8 is an exploded view of the vent located at the distal end of the applicator enclosed by line 8 in FIG. 3;

FIG. 9 is a side plan view of a liquid applicator constructed in accordance with an embodiment of the invention with a portion of the applicator body removed to expose the ampoules being fractured by the lever;

FIG. 10 is a fragmentary cross-sectional view taken generally across line 10—10 of FIG. 2; and FIG. 11 is a fragmentary cross-sectional view taken generally across line 11—11 of FIG. 4.

DETAILED DESCRIPTION OF THE PREFERRED EMBODIMENT

A liquid applicator for applying a desired liquid to a surface, the applicator comprises a hollow body defining an internal chamber to receive at least two elongated ampoules formed of a frangible material and containing the liquid to be applied is described. The liquid applicator further comprises a lever projecting from the body, the lever flexing said body inwardly to fracture the ampoules substantially simultaneously when the lever is depressed toward the body. The liquid applicator further comprises a porous element secured to the body of the applicator and closing off an open end, such that liquid flows through the porous element to be applied to a surface. The following are examples of embodiments of the present invention and are illustrative rather than restrictive.

EXAMPLE 1

With reference FIG. 1, FIG. 2 and FIG. 3 in particular, where like reference numerals identify like elements in the various views, an embodiment of the liquid applicator is illustrated and designated generally by the numeral 10. Liquid applicator 10 generally includes a body 12, and a porous element 16 secured to flange 24 of body 12 and a lever 26.

Two ampoules 14 and 15 are received in body 12. Ampoules 14 and 15 may be used for containing various liquids such as medicaments, cleansing agents, cosmetics, polishes or the like. In the illustrated embodiment, ampoules 14 and 15 contain antiseptic solution to be applied to a patient's skin prior to surgery. Ampoules 14 and 15 are illustrated as elongated cylinders each with a central longitudinal axis. However, it will be appreciated that the principles of the present invention also may be applied to spherical or elongated polygonal ampoules. Furthermore, it will be appreciated that the principles of the present invention may be applied to more than two ampoules.

Preferably, ampoules 14 and 15 are formed of glass, although other materials are entirely within the scope of the present invention. In the illustrated embodiment, ampoules 14 and 15 are placed side by side within body 12. The wall of glass ampoules 14 and 15 is of a thickness sufficient to contain the desired liquid during transport and storage, yet allow ampoules 14 and 15 to be fractured upon the application of localized pressure.

Referring now to FIGS. 4, 5, 6 and 7 body 12 is generally hollow and oval or elliptical in shape and includes axially opposed first and second ends 18, 20. The proximal first end 18 is open and distal second end 20 is closed with cap 19 shown in FIG. 6. Illustrated body 12 is formed of high density polyethylene, although any material exhibiting similar flexibility and integrity may be used. In the illustrated embodiment, body 12 and cap 19 were molded with 100% virgin material DOW, HDPE, Resin # 12454N, as defined in FDA Master File Number 4251. In the preferred embodiment, second end 20 is closed with cap 19, however second end may also be closed during the molding process obviating the need for a cap or the like.

Referring again to FIGS. 1, 2, 3 and 4, body 12 includes an interior wall 21 which defines an internal chamber 22 within body 12. Interior wall 21 is shaped to conform generally to the shape of ampoules 14 and 15 which are received within internal chamber 22. The circumference of interior wall 21 is slightly larger than the outer surface of the two ampoule bodies. Dividing wall 17 of hollow body 12 separates ampoules 14 and 15 and maintains ampoules 14 and 15 within internal chamber 22. Illustrated body 12 is elongated and defines a central longitudinal axis "x".

The thickness of the wall of the applicator may be between 0.040 to 0.080 inches and preferably is approximately 0.060 inches, except thin wall 40. The thickness of the wall of body 12 is reduced around crush area 42. Thin wall 40 may be between 0.020 to 0.040 inches and preferably is 0.030 inches. However, it will be appreciated that different wall sizes may be used within the scope of the embodiment of the invention. Thin wall 40 makes it easier for crush portion 36 of lever 26 to fracture multiple ampoules when lever 26 is depressed. This will be discussed in more detail later.

Body 12 further presents a flange 24 protruding from proximal end 18 along the periphery thereof. In the preferred embodiment, flange 24 is continuously molded to body 12 and is disposed at an angle. Preferably, flange 24 is disposed an angle of 45°, with respect to the central longitudinal axis of the body. It will be appreciated that flange 24 may be disposed at a variety of angles with respect to the central longitudinal axis of body 12. Flange 24 is adapted to support porous element 16, as more fully described below.

Porous element 16, such as a sponge or the like, closes off open end 18 of body 12. Porous element 16 is received on flange 24 and encloses ampoules 14 and 15 within internal chamber 22. Porous element 16 may be formed of felt or an open-celled foam material. In the illustrated embodiment, porous element 16 was formed of SIF-# 3-1000Z felt, (Natural Color Non-Pigmented) Reticulated Polyester Urethane. This felt is hydrophobic and works well with alcohol-based liquids. In another embodiment, AQUAZONE™ polyurethane foam, manufactured by E. N. Murray Co. in Denver, Colo., is used. The AQUAZONE™ foam is hydrophilic and works well with water based liquids.

Porous element 16 is cut from a sheet of foam or felt material having the desired porosity for the liquid to be dispensed. Porous element 16 is preferably generally square in shape although it will be appreciated that the element may be of any desired size and shape which is capable of being supported on flange 24.

In the illustrated embodiment, a woven or non-woven laminate material is laminated to porous element 16. The material laminate material may be a woven or non-woven polyester material. In the illustrated embodiment, Novonnete® SP-64 (3905) Polyester (Non-Woven) was laminated to 0.360"±0.032" SIF-# 3-1000Z felt, (Natural Color Non-Pigmented) Reticulated Polyester Urethane. The laminate material is positioned between porous element 16 and flange 24 of body 12. As such, the laminate material functions to prevent shards of glass from the fractured ampoules from pushing through the porous element during use of the applicator. The laminate material also provides a suitable welding material for securing the porous element in place on the body when an ultrasonic welding operation is used to manufacture the applicator.

In the illustrated embodiment, porous plug 46 is positioned between porous element 16 and ampoules 14 and 15. Porous plug 46 may be an open-celled foam material or felt. In the illustrated embodiment, Novonette® SP-64 (3905) Polyester (Non-Woven) was laminated to 0.360"±0.032" SIF-#3-1000Z Felt, (Natural Color Non-Pigmented) Reticulated Polyester Urethane. Porous plug 46 helps control the rate liquid flows from the body and prevents shards of glass from pushing through porous element 16 during use of the applicator. Porous plug 46 is cut from a sheet of foam or felt material having the desired porosity for the liquid to be dispensed.

Body 12 also includes a lever 26 projecting from the top portion of body 12. However, it will be appreciated that lever 26 may project from any portion of body 12. Lever 26 is any mechanism for fracturing more than one ampoule at substantially the same time. Lever 26, includes hinge portion 38, crush portion 36 and handling portion 34 extending from the distal end of lever 26. Preferably, lever 26 extends outwardly from body 12 at an angle of between 20° and 40° with respect to the central longitudinal axis of body 12. More preferably, lever 26 extends from body 12 at approximately 27° with respect to the central longitudinal axis "x" of body 12. It will be appreciated that lever 26 may be disposed at a variety of angles with respect to the central longitudinal axis of body 12.

In the illustrated embodiment, lever 26 is continuously molded with body 12. It will be understood and appreciated, however, that separately formed levers coupled to the body are contemplated to be within the scope of the present invention.

Handling portion 34 of lever 26 of the illustrated embodiment is spaced between 0.5 and 1.5 inches from body 12. Preferably, handling portion 34 is spaced approximately 1.0 inch from body 12. Handling portion 34 of lever 26 includes a textured outer surface to facilitate handling of applicator 10 and to inhibit slippage from the user's hand during application.

In the illustrated embodiment, lever 26 includes crush portion 36 and hinge portion 38 attached to body 12. It will be appreciated, however, that the principles of the present invention are equally applicable to various other structures for fracturing ampoules 14 and 15, such as multiple crush portions, multiple hinge portions and a crush portion that may be attached or detached to body 12. The hinge portion 38 anchors one end of the lever 26 against the body 12 of the applicator, thus when the lever 26 is depressed, force is transferred into the crush portion 36 of the lever 26. Handling portion 34 of lever 26 presents a gripping area which is significantly larger than the area of crush portion 36. Upon depression of lever 26, crush portion 36, flexes body 12 inwardly at thin wall 40, thereby localizing the forces effected by depressing lever 26 toward body 12 and enhancing fracturing of ampoules 14 and 15 as more fully described below.

Several features of lever 26 of the illustrated embodiment enhance the ability to fracture at least two ampoules at the same time including: the thickness of lever 26, the curvature of lever 26, support rib 37 (as illustrated in FIG. 2), the thickness of hinge portion 38 and the width of crush portion 36. The thickness of lever 26 is approximately 0.080 to 0.15 inches and preferably is 0.11 inches. In the illustrated embodiment, lever 26 is approximately 2.35 inches long. Hinge portion 38 of the illustrated embodiment is thinner than the rest of lever 26. Hinge portion 38 is approximately 0.040 to 0.080 inches thick, preferably 0.060 inches thick. The curvature of lever 26 and support rib 37 increase the leverage of handling portion 34 of lever 26 making it easier for the user to fracture two ampoules substantially simultaneously.

The ratio of the width of crush portion 36 to the width of ampoules 14 and 15 side by side is important with respect to reliable breakage of ampoules 14 and 15. In the illustrated embodiment, the width of the crush portion 36 had to be at least approximately ⅕ the width of the two ampoules side by side to produce breakage of the ampoules almost simultaneously. The width of the two ampoules side by side was approximately 1.03 inches. The minimum width of the crush portion of the lever that produces breakage of the ampoules almost simultaneously was 0.200 inches. Thus, a length aspect ratio for reliable ampoule break was 1.03/0.200 or 5.15. All of these features, either singularly or in combination, along with thin wall 40, help enhance the ability of the lever to break multiple ampoules at the same time. In the preferred embodiment of the present invention, the crush portion of the lever was 0.675 inches. The width of the two ampoules side by side is approximately 1.03 inches. Thus, the preferred length aspect ratio is 1.03/0.675 or 1.53.

With reference to FIG. 7 and FIG. 8, vent 56 of the illustrated embodiment is shown. Vent 56 is located at distal end 20 of body 12. Vent 56 is a small cut out portion of body 12 allowing air to flow from internal chamber 22 of body 12 to the outside of body 12 and vice versa. This is accomplished by a small cut out portion of body 12 starting on the outside of body 12, going over the lip of body 12 and continuing inside body 12. Internal cut out portion 54, external cut out portion 50 and cut out lip 52 allow air to flow in and out of internal chamber 12 of body 12 underneath cap 19. Cap 19 entirely seals off internal chamber 22 except for cut out vent 56.

With reference to FIG. 9 and FIG. 11, restraint element 44 is positioned between ampoules 14 and 15 and porous plug 46. Restraint element 44 allows liquid to flow from body 12, through porous plug 46 and into porous element 16. Restraint element 44 restrains ampoules 14 and 15 in a position to facilitate proper breaking. Restraint element 44 holds the ends of ampoules 14 and 15 near crush point 42 so that the ends of ampoules are properly broken and do not restrict the flow of liquid. Restraint element 44 may take a variety of shapes depending on the type of liquid to be applied. In the illustrated embodiment, restraint element 44 has two fan-shaped openings as may be seen in FIG. 11.

With reference to FIG. 5, 9, 10 and 11, in use, applicator 10 presents a hand-held liquid applicator wherein lever 26 is depressed to release the desired liquid contained within ampoules 14 and 15 therein for application to a surface. Applicator 10 of the illustrated embodiment is grasped by one hand of a user. The bottom of body 12 is grasped with the palm and fingers of user, the user's fingers wrap around the bottom and side of the body 10 so the tips of the user's fingers rest on the top of body 12. The thumb of the same hand is positioned on handling portion 34 of lever 26 allowing for single-handed operation. The user depresses lever 26 toward body 12 to fracture ampoules 14 and 15. The movement of lever 26 is transferred by crush portion 36 to thin wall 40 of body 12 to deform body 12 inwardly and exert discrete localized fracturing forces against ampoules 14 and 15. Lever 26 provides an action that gains mechanical advantage as lever 26 is depressed toward body 12. Accordingly, if the user has limited gripping strength, or if the wall of the ampoule is exceptionally thick, the lever ensures fracturing of the ampoules.

Once lever 26 has been sufficiently depressed, the resulting forces fracture ampoules 14 and 15 almost simultaneously, thus releasing the liquid contained in each ampoule. Once ampoules 14 and 15 are fractured, the released liquid saturates porous plug element 46 which controls the rate of the flow and then the liquid saturates porous element 16. Consequently, body 12 essentially functions as a reservoir of the desired liquid. When the applicator is manipulated for scrubbing with the distal end oriented away from the surface to be scrubbed and the porous element oriented toward the surface as shown in FIG. 1, the liquid will flow from the fractured ampoule under the force of gravity down body 12, through porous plug 46 the through open end 18 and through porous element 16. Thereafter, application of the liquid is accomplished by bringing porous element 16 into contact with the desired surface. The user may then use a painting or scrubbing motion to apply the liquid to the surface. The entire process of fracturing ampoules 14 and 15 and applying the liquid to a desired surface is achieved with the use of only one hand of the user.

EXAMPLE 2

In this embodiment, the liquid applicator 10 is constructed to house two 13 ml ampoules. The thickness of the walls of the 13 ml ampoules is 0.3 mm. It will be understood and appreciated, however, that ampoules of various sizes with various wall widths may be utilized and such is contemplated to be within the scope of the present invention. In the illustrated embodiment, the distance between the lateral line defined by the most upwardly positioned portion of the flange and the distal end of the handling portion of the lever is approximately 3.75 inches. It will be understood and appreciated, however, that this distance will vary based upon the size of the applicator and ampoule utilized. Such variations are contemplated to be within the scope of the present invention.

EXAMPLE 3

During formation of the applicator, the porous element is welded to the applicator body in three steps. First, the flange of the body is pre-heated with the aid of an infrared heater that is set at a temperature ranging between 620 and 625° F. The flange and the body are held in place with a nesting fixture, and a gap between the flange and the heating element is set to 0.125". The flange is heated for approximately fifteen seconds to achieve a temperature of approximately 150 to 160° F. Next, the porous plug is manually inserted into the applicator body while the flange area is still warm. Finally, while the pre-heated body and flange containing the porous plug are still in the nesting fixture, a porous element is centered onto the flange. The flange and the porous element are bonded together with a sonic welding machine. It will be appreciated that other suitable securing expedients could be employed in place of the ultrasonic welding operation. For example, the porous element could be secured in place by an adhesive or stitching, or by heat sealing or chemically bonding the element in place. Such alternative securing expedients are contemplated to be within the scope of the present invention. The completed applicator body containing the porous plug with the porous element secured to the flange is removed from the fixture. Two 13 ml ampoules are inserted through the distal opening into the applicator body. The cap is inserted into position using a customized pneumatic press and nesting fixture. Finally, the cap is compressed into its final position closing the applicator body at the distal end.

Constructed and operated as previously described, this invention provides a hand-held liquid applicator of quality construction having a body with a lever that may be depressed toward the body to fracture at least two ampoules of liquid contained within the body. Further, this invention provides a disposable liquid applicator which permits single-handed operation in order to free the second hand of the user for use in assisting application of the liquid to the desired area. The liquid applicator of the present invention also is simple to construct and assemble and, therefore, may be manufactured more economically than prior art applications. From the foregoing, it will be seen that this invention is one well adapted to attain all the ends and objects hereinabove set forth together with other advantages which are obvious and which are inherent in the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. A liquid applicator for applying a desired liquid to a surface, the applicator comprising:
    at least two elongated ampoules formed of a frangible material and containing liquid to be applied;
    an elongated hollow body, said body defining an internal chamber adapted to receive said ampoules;
    a lever projecting from said body, said lever flexing said body inwardly to fracture said ampoules substantially simultaneously when the lever is squeezed toward the body; and
    a porous element secured to said body and closing off an open end thereof, such that liquid flows through said element when said ampoules are fractured.

2. The liquid applicator of claim 1, wherein the lever is comprised of a hinge portion, crush portion and handling portion.

3. The liquid applicator of claim 2, wherein the body has a central longitudinal axis.

4. The liquid applicator of claim 3, wherein the lever extends at an angle of between 20 degrees and 40 degrees with respect to the central longitudinal axis of the body.

5. The liquid applicator of claim 2, wherein the crush portion of the lever flexes the body inwardly to fracture said ampoules.

6. The liquid applicator of claim 2, further comprising a thin wall portion of the body where the body flexed inwardly to fracture said ampoules.

7. The liquid applicator of claim 2, wherein the lever is curved.

8. The liquid applicator of claim 7, wherein the lever further comprises a support rib.

9. The liquid applicator of claim 8, wherein the hinge portion of the lever is thinner than the rest of the lever.

10. The liquid applicator of claim 9, wherein the handling portion of the lever presents a gripping area that is larger than the area of the crush portion of the lever.

11. The liquid applicator of claim 10, wherein the handling portion has a textured outer surface to facilitate handling.

12. The liquid applicator of claim 1, wherein the body has axially opposed open and closed ends.

13. The liquid applicator of claim 12, wherein the closed end is closed with a cap.

14. The liquid applicator of claim 13, further comprising:
    a vent for allowing air to flow from the internal chamber of the body to the outside of the body.

15. The liquid applicator of claim 14, wherein the vent comprises an internal cut out portion of the body and an external cut out portion of the body.

16. The liquid applicator of claim 1, further comprising a porous plug positioned between the porous element and the two or more ampoules to control the rate of flow of the liquid.

17. The liquid applicator of claim 16, further comprising a restraint element positioned between the ampoules and the porous plug.

18. A liquid applicator for applying liquid to a surface, the applicator comprising:
    at least two elongated ampoules formed of a frangible material and containing the liquid to be applied;

an elongated hollow body, said body defining an internal chamber adapted to receive said ampoules;

a mechanism attached to said body, the mechanism having the capability of flexing said body inwardly to fracture said ampoules at substantially the same time; and a porous element secured to said body and closing off an open end thereof, such that liquid flows through said element when said ampoules are fractured.

19. The liquid applicator of claim 18, further comprising a porous plug positioned between the porous element and the two or more ampoules to control the rate of flow of the liquid.

20. The liquid applicator of claim 18, further comprising a restraint element.

21. A method of making a liquid applicator, the applicator shaped for receiving at least two frangible ampoules containing a liquid to be applied, the method comprising:

providing a hollow elongated body having axially opposed open and closed ends and being adapted to receive the ampoules;

coupling to the body a lever, said lever projecting from said body, said lever having the capability to flex said body inwardly to fracture said ampoules substantially simultaneously when the lever is squeezed toward the body; and securing to said body a porous element, said element positioned to close of said open end of said body, such that liquid flows into said body and through said element when the ampoules are fractured.

* * * * *